(12) United States Patent
Chae et al.

(10) Patent No.: US 7,417,171 B2
(45) Date of Patent: Aug. 26, 2008

(54) METHOD FOR PREPARING AN AROMATIC DIALDEHYDE AND MANUFACTURING SYSTEM FOR THE SAME

(75) Inventors: Jong Hyun Chae, Daejeon (KR); Won Ho Lee, Daejeon (KR); Dong Il Lee, Gyeonggi-do (KR); In Kyu Park, Daejeon (KR); Yong Jin Choe, Daejeon (KR); Sung Kyu Lee, Daejeon (KR); Yeong Dae Kim, Daejeon (KR); Jong Suh Park, Chungnam (KR); Seong Hoon Kang, Daejeon (KR)

(73) Assignee: LG Chem, Ltd., Seoul (KR)

( * ) Notice: Subject to any disclaimer, the term of this patent is extended or adjusted under 35 U.S.C. 154(b) by 0 days.

(21) Appl. No.: 11/637,674

(22) Filed: Dec. 13, 2006

(65) Prior Publication Data

US 2007/0135659 A1    Jun. 14, 2007

(30) Foreign Application Priority Data

Dec. 14, 2005   (KR) .................. 10-2005-0123140
Jul. 19, 2006   (KR) .................. 10-2006-0067396

(51) Int. Cl.
*C07C 45/27* (2006.01)
*C07C 45/90* (2006.01)

(52) U.S. Cl. .................. 568/431; 568/432; 568/434

(58) Field of Classification Search .................. None
See application file for complete search history.

(56) References Cited

U.S. PATENT DOCUMENTS

| 3,597,483 | A | 8/1971 | Haarer et al. |
| 3,597,485 | A | 8/1971 | Brill |
| 4,017,547 | A | 4/1977 | Simmons et al. |
| 5,324,702 | A | 6/1994 | Yoo et al. |
| 6,458,737 | B1 | 10/2002 | Kishimoto et al. |

FOREIGN PATENT DOCUMENTS

GB        1217796        12/1970

*Primary Examiner*—Sikarl A Witherspoon
(74) *Attorney, Agent, or Firm*—McKenna Long & Aldridge LLP

(57) ABSTRACT

The present invention relates to a method for preparing an aromatic dialdehyde, comprising, a) a step of gas phase oxidation reaction for preparing aromatic dialdehyde from dimethyl benzene; b) a step of separation for selectively recovering crude aromatic dialdehyde of molten phase from the reaction product of the step (a); and c) a step of purification for obtaining highly pure aromatic dialdehyde by purifying said crude aromatic dialdehyde, and a manufacturing system used for the preparation method. The method for preparation of the aromatic dialdehyde according to the present invention is simple, effective, and advantageous in that highly pure aromatic dialdehyde can be continuously prepared.

14 Claims, 2 Drawing Sheets

METHOD FOR PREPARING AN AROMATIC DIALDEHYDE AND MANUFACTURING SYSTEM FOR THE SAME

This application claims the benefit of Korean Patent Application No. 10-2005-0123140, filed on Dec. 14, 2005 and Korean Patent Application No. 10-2006-0067396, filed on Jul. 19, 2006, which are hereby incorporated by reference for all purposes as if fully set forth herein.

TECHNICAL FIELD

The present invention relates to a method for preparing an aromatic dialdehyde and a manufacturing system for the same. Specifically, the present invention relates to a method for continuously preparing a highly pure aromatic dialdehyde, and a manufacturing system for the same.

BACKGROUND ART

An aromatic dialdehyde, particularly terephthalaldehyde, is a bifunctional compound which has been noted as a new basic material having various uses. For example, it is used as a basic material for liquid crystals; conductive polymers; or high temperature engineering polymers such as polyimine, polystyrylazine or polybenzimidazole, etc., and also is applied to fluorescent brightening agents or specialty polymers. Further, it is applied as a basic material for specialty monomers such as cyclohexanedimethanol, p-hydroxybenzoic acid, hydroquinone, p-hydroxymethylbenzoic acid, etc.

Terephthalaldehyde is typically synthesized by a liquid phase reaction from di- or tetrachlorinated side chain derivatives of p-xylene. However, it is not easy to produce it in large scale, and so has some limitations to be developed for various uses. However, a method for preparing terephthalaldehyde by one step gas phase oxidation reaction from p-xylene was developed and commercialized, thereby receiving more interests for its production and use in a large scale.

U.S. Pat. No. 3,597,485 describes a method for preparing terephthalaldehyde through one step gas phase oxidation reaction of p-xylene by using a catalyst consisting of tungsten and molybdenum.

U.S. Pat. No. 4,017,547 describes a catalyst consisting of tungsten, molybdenum, and bismuth.

U.S. Pat. No. 5,324,702 describes a catalyst wherein iron, zinc, vanadium, molybdenum, tungsten, etc. are incorporated to deboronated borosilicate crystal molecular sieve via chemical vapor deposition.

Also, U.S. Pat. No. 6,458,737 B1 discloses a multi-component oxide catalyst comprising tungsten and antimony.

However, the above prior arts merely disclose catalysts used for preparing terephthalaldehyde by one step gas phase oxidation reaction, or the preparation method per se, and provide no information on the separation or purification method for obtaining highly pure terephthalaldehyde. When the above prior catalysts are used, the desired terephthalaldehyde is obtained in a low yield, or in a low selectivity with a high yield, and so its separation and purification are not easy. Further, due to the use of multi-component oxide complex, it is not easy to prepare a catalyst having homogenous composition and property. Furthermore, since the catalysts of the prior arts include some components having low thermal stability, their life is short, and so they have some limitations for industrial application.

DISCLOSURE OF THE INVENTION

The present invention has been developed to solve the above mentioned problems. Thus, one object of the present invention is to provide a method for preparing an aromatic dialdehyde wherein a highly pure aromatic dialdehyde can be continuously obtained without using an organic solvent in the purification step.

Another object of the present invention is to provide a manufacturing system used for the above method.

The present method for preparing an aromatic dialdehyde comprises, a) a step of gas phase oxidation reaction for preparing an aromatic dialdehyde by oxidizing dimethylbenzene in a gaseous phase; b) a step of separation for selectively recovering crude aromatic dialdehyde of molten phase by cooling and condensing a reaction product from the gas phase oxidation reaction, and heating to melt it down; and c) a step of purification for obtaining highly pure aromatic dialdehyde by purifying the crude aromatic dialdehyde.

The present invention will be more specifically explained below.

Terephthalaldehyde should be obtained in a highly pure state to be used as a basic material for high temperature engineering polymer compounds, fine chemicals, etc. exemplified in the background art. However, as mentioned in the background art, highly pure terephthalaldehyde can hardly be obtained only by conventional methods using a liquid phase reaction or one step gas phase oxidation reaction, without any additional purification step.

The crude terephthalaldehyde after the gas phase oxidation reaction contains various impurities, and so a separate purification step is needed to give highly pure terephthalaldehyde. Particularly, to produce highly pure terephthalaldehyde in a large scale by one step gas phase oxidation method, it is preferable that the reaction-separation-purification steps are carried out in a continuous manner.

The method for preparing an aromatic dialdehyde according to the present invention is designed for gas phase oxidation reaction of the first step, and subsequent separation and purification to be continuously carried out. Specifically, it comprises, a) a step of gas phase oxidation reaction for preparing the aromatic dialdehyde by oxidizing dimethylbenzene in a gas phase and in the presence of a solid catalyst; b) a step of separation for selectively recovering crude aromatic dialdehyde of molten phase by cooling and condensing a reaction product from the gas phase oxidation reaction in a switch condenser, and heating to melt it down; and c) a step of purification for obtaining highly pure aromatic dialdehyde by purifying the crude aromatic dialdehyde in a distillation column.

Each step of the present method for an aromatic dialdehyde is explained below.

A. Step of Gas Phase Oxidation Reaction

In the present invention, aromatic dialdehyde is prepared by oxidizing dimethylbenzene in a gas phase and in the presence of a solid catalyst. A gas phase reaction mixture of dimethylbenzene and a gas phase oxidant is passed through the inside of a reactor which is filled with the solid catalyst to produce aromatic dialdehyde by a partial oxidation reaction.

Here, dimethylbenzene is preferably one or more selected from the group consisting of o-xylene, m-xylene and p-xylene, and the gas phase oxidant is preferably oxygen or oxygen-containing air.

In the gas phase oxidation reaction, it is preferable that dimethylbenzene to be introduced into the inside of the reactor is used in the concentration of 0.5 to 1% by volume with respect to the gas phase reaction mixture containing dimethylbenzene and gas phase oxidant. The amount of aromatic dialdehyde produced may be reduced when the concentration of dimethylbenzene is less than 0.5% by volume, and there is a risk of explosion during the reaction procedure when the concentration is more than 1% by volume.

Also, in the gas phase oxidation reaction, the concentration of oxygen among the gas phase reaction mixture needs to be appropriately controlled depending on the kind of catalyst and reaction condition since it may affect the activity and selectivity of the catalyst.

Thus, either a gas mixture having a low concentration of oxygen made by adding some inert gas to the gas phase oxidant, or a gas mixture having a high concentration of oxygen made by adding oxygen to air, may be used.

As the concentration of oxygen in the gas phase reaction mixture increases, the conversion rate of the partial oxidation reaction of dimethylbenzene increases. However, when the concentration exceeds a certain range, the selectivity of aromatic dialdehyde may decrease due to facilitation of complete oxidation reaction. Also, when the concentration of oxygen in the gas phase reaction mixture increases extraordinarily, the risk of explosion also increases. Thus, the concentration of oxygen in the gas phase reaction mixture is preferably maintained at 15 to 30% by volume.

It is preferable to use the conventional fixed bed reactor for the gas phase oxidation reaction. In some cases, a fluid bed reactor may be used.

The oxidation reaction of dimethylbenzene is an exothermic reaction of releasing a large amount of heat, and so the heat should be removed. If the heat is not properly removed, the temperature gradient inside the reactor increases, whereby the selectivity of the desired product of aromatic dialdehyde may be reduced. Further, a run-away phenomenon due to the heat of reaction may cause a fatal damage to the reactor and catalyst.

For a fixed bed reactor, it is preferable to use a multiple tube reactor equipped with a jacket through which a molten salt is circulated, to control the heat of reaction. Said molten salt may be circulated either co-currently or counter-currently with respect to the reaction mixture. Only, it is preferable to circulate the molten salt counter-currently to maintain the temperature of catalyst layer in the reactor constant.

In the fluid bed reactor, mixing of reactants and catalyst may be well done, and the removal of heat may be easily carried out. Thus, the fluid bed reactor has the merit of not using a additional device for controlling the heat of reaction. Since the temperature in the fluid bed reactor can be more constantly maintained, it has the additional advantage that the selectivity of the desired product is increased. However, the reaction procedure may become complicated, and some loss of catalyst may occur due to working characteristics thereof.

The gas phase oxidation reaction is preferably carried out in the presence of a solid catalyst comprising tungsten, molybdenum, or a mixture thereof as an active component.

Particularly preferably, the solid catalyst comprises as an active component the compound of the following formula (1):

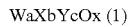

wherein,

W represents a tungsten atom,

X represents one or more alkali metals selected from the group consisting of Li, Na, K, Rb, and Cs, preferably one or more alkali metals selected from the group consisting of Rb, Cs, Na, and K, Y represents one or more elements selected from the group consisting of Fe, Co, Ni, Cu, Mn, Re, Cr, V, Nb, Ti, Zr, Zn, Cd, Y, La, Ce, B, Al, Sn, Mg, Ca, Sr, and Ba, preferably one or more elements selected from the group consisting of Fe, Ce, Ni, Co, Sr, La, Cu, Zn and Zr, O stands for an oxygen atom, a, b, c and x each represent the atomic number of W, X, Y and oxygen atom, respectively, the ratio of a:b:c is 12:0.001~1:0~5, preferably 12:0.005~1:0~2, more preferably 12:0.01~0.5:0~1, and x is a value determined by the oxidation state of W, X, and Y In the above, if b that is the ratio of component X is less than 0.001, the selectivity of the final product may be decreased, and if b is more than 1, the conversion rate may be rapidly decreased. Also, if c that is the ratio of component Y is more than 5, the selectivity of the final product may be decreased.

The present invention is characterized in adding a very small amount of alkali metal component into tungsten oxide to increase the selectivity and yield of aromatic aldehyde and to improve the thermal stability of the catalyst. The catalyst for partial oxidation represented by the above formula (1) comprises a binary system comprising tungsten and one kind of alkali metal, for example, $W_{12}Rb_{0.02}$, $W_{12}Rb_{0.03}$, $W_{12}Cs_{0.02}$, $W_{12}Cs_{0.03}$, $W_{12}Na_{0.025}$, or $W_{12}K_{0.02}$; a tertiary system comprising tungsten, an alkali metal and a third component, for example, $W_{12}Rb_{0.02}Fe_{0.05}$, $W_{12}Rb_{0.02}Fe_{0.2}$, $W_{12}Rb_{0.2}Fe_{0.5}$, $W_{12}Rb_{0.02}Ce_{0.3}$, $W_{12}Rb_{0.02}Ni_{0.1}$, $W_{12}Rb_{0.02}Co_{0.1}$, $W_{12}Rb_{0.02}Sr_{0.1}$, $W_{12}Rb_{0.02}La_{0.3}$, $W_{12}Rb_{0.02}Cu_{0.1}$, $W_{12}Rb_{0.02}Zn_{0.1}$, or $W_{12}Rb_{0.02}Zr_{0.1}$; and a tertiary system comprising tungsten and two kinds of alkali metals, for example, $W_{12}Rb_{0.01}K_{0.01}$, $W_{12}Rb_{0.01}Cs_{0.01}$, or $W_{12}Rb_{0.015}Cs_{0.005}$.

The catalyst for partial oxidation of the present invention can be used in the form of powder, particle, pellet, sphere, or ring, or can be supported on a fire-resistant inorganic support in order to improve the activity, selectivity or physical durability. It is preferable for the support to be in the form of pellet, sphere, or ring. The solid catalyst in the form of pellet, sphere, or ring is suitable for the fixed bed reactor, and that in the form of powder or particle is suitable for the fluid bed reactor.

Typical examples of such fire-resistant inorganic support are alumina such as α-alumina, silica, titania, zirconia, silicon carbide, etc. In case the active component of the above formula (1) is supported on a fire-resistant inorganic support, the loading amount is at least 5 wt %, preferably at least 12 wt %, and more preferably at least 15~90 wt %, of the sum of the support weight plus the catalytic active component weight, in view of the objects of the present invention. If the amount is below 5 wt %, the required reaction activity and selectivity of terephthalaldehyde cannot be attained. The loading amount may depend on the pore volume of the support, and the support with larger pore volume is advantageous in that the loading amount can be increased.

Also, according to the present inventors' experiments, the conversion rate is improved, but the selectivity is decreased, as the surface area of the support is increased. From their several experiments, it was shown that a support having the surface area of 0.5 m²/g or less, preferably 0.1 m²/g or less, more preferably in the range of 0.005 m²/g to 0.05 m²/g, is advantageous in view of the conversion rate of methylbenzenes and the selectivity of terephthalaldehyde since the complete oxidation of methylbenzenes and side reactions can be prevented. Within the above range, the conversion rate increases, as the surface area increases.

Further, a support having an average pore size of at least 10 μm, preferably at least 50 μm, is advantageous in obtaining the desired high selectivity of terephthalaldehyde.

The shape of inorganic carrier or catalyst prepared thereby is not particularly limited, and sphere, pellet, ring, honeycomb, etc. can be selectively used. Further, not only molded products but also oxide or hydroxide powders, gels, sols, etc. can be selectively used.

The conventional reaction temperature of the gas phase oxidation reaction may be determined depending on main component of the catalyst, and ranged preferably from 350 to 600° C. Increase of the conversion rate of the reactants may be limited when the temperature is lower than 350° C. When the temperature is higher than 600° C., excess oxidation may occur to cause the conversion of the desired product aromatic dialdehyde to COx, and loss thereof.

More preferably, the temperature of the gas phase oxidation reaction ranges from 450 to 600° C. when a solid catalyst having tungsten as the main component is used, and from 350 to 450° C. when a solid catalyst having molybdenum as the main component is used. In case a solid catalyst having tungsten as the main component is used, the temperature of lower than 450° C. of the gas phase oxidation reaction may reduce the conversion rate of dimethylbenzene to give some limit in increasing the yield of aromatic dialdehyde, and the temperature of higher than 600° C. may cause excess oxidation to result in a low yield of aromatic dialdehyde. Likewise, in case a solid catalyst having molybdenum as the main component is used, the temperature of lower than 350° C. of the gas phase oxidation reaction may reduce the conversion rate of reactants, and that of higher than 450° C. may cause excess oxidation to result in a loss of product.

Also, the reaction pressure of the gas phase oxidation reaction ranges preferably from 0.01 to 1 atm (gauge pressure). A vacuum pump is additionally required to carry out the reaction when the pressure is lower than 0.01 atm, and the yield of the reaction product, aromatic dialdehyde, may be reduced when the pressure is higher than 1 atom.

The flow rate of the reaction mixture containing dimethylbenzene and gas phase oxidant is preferably controlled to the range of from 1000 to 50000 $hr^{-1}$ in the gas phase oxidation reaction. The productivity of preparing the aromatic dialdehyde decreases when the flow rate of the reaction mixture is lower than 1000 $hr^{-1}$, and the yield of aromatic dialdehyde is reduced when the flow rate is higher than 50000 $hr^{-1}$.

The above explained gas phase oxidation reaction gives one or more aromatic dialdehydes selected from the group consisting of phthaldialdehyde, isophthalaldehyde and terephthalaldehyde.

However, benzaldehyde, tolualdehyde, carboxybenzaldehyde, aromatic dicarboxylic acid, etc are also obtained as side products of the reaction, and such side products as CO or $CO_2$ may be produced by the complete oxidation reaction.

The product of the gas phase oxidation reaction containing both aromatic dialdehyde and side products is discharged from the outlet of the reactor with $H_2O$ and excess unreacted residual air to be transferred to a switch condenser as a separation system.

B. Separation Step

In the method for preparing an aromatic dialdehyde according to the present invention, the step of separation is to selectively condense the aromatic dialdehyde from the product of said gas phase oxidation reaction, melt, and separate the condensed product.

Preferably, the separation step is carried out by using a switch condenser of which the temperature control is possible, and more preferably is carried out by using two or more switch condensers in a continuous manner wherein cooling and heating are repeated in turn.

The capacity of the switch condenser plays a very important role in determining the efficacy of the present method for preparing an aromatic dialdehyde. The recovery rate of the aromatic dialdehyde depends on how completely the aromatic dialdehyde can be condensed to a solid and separated in the condenser.

It is preferable for the switch condenser to include a tube bundle equipped with a heat transfer fin. The cooling and heating of the switch condenser is preferably achieved by passing a heat transfer oil through the tube bundle. The heat transfer oil is classified into cooling medium and heating medium. In the above cooling and heating, the same heat transfer oil may be used in turn as a cooling medium and a heating medium, but the operation is easy when the heating medium and the cooling medium are used separately. Also, cooling water and steam may be used instead of the heat transfer oil, but it is more effective to use the heat transfer oil.

Under a cooling mode wherein the cooling medium is circulated through the inside of the tube bundle equipped with a fin, a part of the reaction product containing aromatic dialdehyde is condensed on the surface of the tube bundle and recovered as a solid. The resulting solid product melts during a heating mode wherein the heating medium is circulated through the inside of the tube bundle, and transferred to a storage tank.

Preferably, the temperature of the switch condenser at the cooling mode ranges from 5 to 70° C., and that of the switch condenser at the heating mode ranges from 110 to 200° C. Energy costs increase, and there is a risk that other impurities are additionally condensed together with the aromatic dialdehyde when the temperature of the cooling mode is lower than 5° C. And, the recovery rate of the aromatic dialdehyde decreases when the temperature exceeds 70° C. Further, the aromatic dialdehyde condensed to a solid cannot be molten when the temperature of heating mode is lower than 110° C., and loss of the product due to the additional reaction of the molten crude aromatic dialdehyde may increase when the temperature exceeds 200° C.

As the cooling medium oil is replaced with the heating medium oil at the initial stage of the heating mode of the switch condenser, a lot of energy (i.e., steam) is consumed for heating the heat transfer oil. Thus, it is preferable to connect an additional heat storage tank to the heating medium oil system for the prevention of consumption peak of steam used as an energy source of the process, and the constant control.

It is preferable to increase the recovery rate of the aromatic dialdehyde by the switch condenser to 98% or more, and more preferable to 99% or more. Said recovery rate means the ratio of the aromatic dialdehyde condensed to a solid in a condenser and recovered to the aromatic dialdehyde produced by the gas phase oxidation reaction. Here, the aromatic dialdehyde not condensed to a solid goes out of the reaction product together with the non-condensable gas (i.e., nitrogen, oxygen, CO, $CO_2$, etc.) in the product.

When oxygen is included in the inside of the condenser during the heating mode operation (melting process), the molten aromatic dialdehyde may react with oxygen to be converted into carboxybenzaldehyde, aromatic dicarboxylic acid, etc. Thus, all the processes after the switch condenser should be operated under the condition that the molten aromatic dialdehyde does not contact oxygen. Therefore, it is preferable to purge the inside of the condenser with inert gas.

The inert gas that can be used here is not particularly limited, but it is preferable to use one or more inert gases selected from the group consisting of nitrogen, argon, helium and $CO_2$.

To continuously operate the separation step by using a switch condenser, the switch condenser should be two or more for continuous switching. That is, the switch condenser is operated in such a manner that cooling cycle and melting cycle are repeated in turns. Thus, while the aromatic dialdehyde is recovered as a solid in one condenser of cooling cycle, the solid aromatic dialdehyde recovered from the previous cooling cycle is molten to a liquid in the other condenser of melting cycle. Therefore, it is preferable to use two or more switch condensers, and more preferable to use three or more ones for the continuous and efficient operation.

The switch condenser may be sorted out into up-flow and down-flow depending on the positions of inlet and outlet. In a condenser in the form of up-flow, the gas phase reaction product is introduced from the bottom, passed through the inside tube bundle, and discharged to the top. And, in a condenser in the form of down-flow, the gas phase reaction product is introduced from the top, and discharged to the bottom.

The molten aromatic dialdehyde obtained from the above separation step contains a part of the side products produced from the gas phase oxidation reaction of dimethylbenzene, and so its purity is not so high.

Thus, it is called crude aromatic dialdehyde, and this crude aromatic dialdehyde may be purified to give highly pure aromatic dialdehyde.

C. Purification Step

The purification step in the present method for preparing aromatic dialdehyde is to purify the crude aromatic dialdehyde to give highly pure aromatic dialdehyde.

In the present purification, it is preferable to use a distillation device comprising, i) the first distillation column to remove impurities having a low boiling point, and ii) the second distillation column connected with the first column in a series to recover the aromatic dialdehyde.

The removal of impurities having a low boiling point by using the first distillation column, and the recovery of aromatic dialdehyde by using the second distillation column are carried out continuously.

In the first distillation column, the compounds having a low boiling point contained in the crude aromatic dialdehyde are removed from the top of the column. The temperature of the top of the first column preferably is maintained at 74~79° C., and that of the bottom is maintained at 170~175° C. The impurities having a low boiling point may not be easily removed when the temperature of the top of the first column is lower than 74° C., and some loss of aromatic dialdehyde may occur from the top when the temperature exceeds 79° C. Also, when the temperature of the bottom is lower than 170° C., some compounds having a low boiling point may fall down to the bottom to reduce the purity of aromatic dialdehyde. When the temperature of the bottom exceeds 175° C., there is a risk that aromatic dialdehyde together with the compounds having a low,boiling point are transferred to the top.

The crude aromatic dialdehyde collected at the bottom of the first distillation column is transferred to the second distillation column, and recovered as highly pure aromatic dialdehyde at the top of the second column. The residual compounds piled up at the bottom of the second column are discharged to the outside. Here, it is preferable to maintain the temperature of the top of the second distillation column at 165~170° C., and that of the bottom at 195~200° C. The aromatic dialdehyde may not be easily recovered when the temperature of the top of the second column is lower than 165° C., and the purity of the aromatic dialdehyde may decrease due to the migration of the compounds having a high boiling point to the top when the temperature exceeds 170° C.

Further, some compounds having a low boiling point may be included in the lower part of the top when the temperature of the bottom is lower than 195° C., and there is a risk that the impurities having a high boiling point are recovered with the aromatic dialdehyde when the temperature exceeds 200° C.

The highly pure aromatic dialdehyde recovered from the top of the second distillation column is transferred to the storage tank in molten state. It is preferable to purge the storage tank with inert gas to prevent the deterioration of the aromatic dialdehyde due to oxidation.

The present invention further provides a manufacturing system for preparing the aromatic dialdehyde, comprising, a) a part for gas phase oxidation reaction, b) a part for separation, and c) a part for purification Wherein, a) the part for oxidation reaction comprises a feeder of dimethyl benzene, a feeder of gas phase oxidant, and a reactor where the gas oxidation reaction occurs, b) the part for separation comprises a switch condenser, and c) the part for purification comprises the first distillation column for removing the impurities having a low boiling point and the second distillation column for recovering the highly pure aromatic dialdehyde.

Hereinafter, the manufacturing system according to the present invention will be explained in more detail with referring to the figures.

FIG. 1 is a scheme of the manufacturing system for preparing the aromatic dialdehyde according to the present invention. However, FIG. 1 is only an example for explaining the manufacturing system of the present invention, and the manufacturing system is not restricted to the constitution of FIG. 1.

As shown in FIG. 1, the manufacturing system of the present invention is roughly divided into a part for gas phase oxidation reaction (100), a part for separation (200), and a part for purification (300).

The part for oxidation reaction (100) comprises a mixer (30) that mixes dimethylbenzene and gas phase oxidant provided from the feeder of dimethylbenzene (31) and the feeder of gas phase oxidant (32), and a reactor (40) wherein the gas phase oxidation reaction of the mixture provided from the mixer is carried out. The reactor (40) is preferably in the form of a fixed bed catalyst reactor consisting of multi tubes for controlling the reaction temperature by a molten salt, and also preferably further comprises a circulator or pump (41) for circulating the molten salt with a jacket for molten salt in the inside of the reactor.

Also, the part for separation (200) of the present invention comprises two or more switch condensers (50), an incinerator (60) for incinerating residual gas phase reactants, and a storage tank (70) for storing the crude aromatic dialdehyde obtained from the switch condenser.

The part for purification (300) of the present invention comprises the first distillation column (80) for removing the impurities having a low boiling point and the second distillation column (90) for recovering the highly pure aromatic dialdehyde, wherein gas stream from the top of the first column (80) is fed into a partial condenser (81) wherein the impurities having a low boiling point are removed and the remaining part is condensed, and then refluxed into the top of the first column (80); and a certain amount of the residue compound in the first column (80) after removing the low boiling point impurities is circulated through a re-boiler (82) into the bottom of the first column (80) for maintaining desired purity, while remaining amount of the residue compound is transferred to the second distillation column (90) by pressure difference.

The top of the second distillation column (90) is equipped with a condenser (91) refluxing a certain amount thereinto for recovering aromatic dialdehyde, and the bottom thereof is equipped with a re-boiler (92) circulating a certain amount thereinto for removing the impurities having a high boiling point.

The aromatic dialdehyde prepared according to the present method is one or more selected from the group consisting of phthaldialdehyde, isophthalaldehyde and terephthalaldehyde, whose purity is 99.5 wt % or more.

BEST MODE FOR CARRYING OUT THE INVENTION

Figure 1:
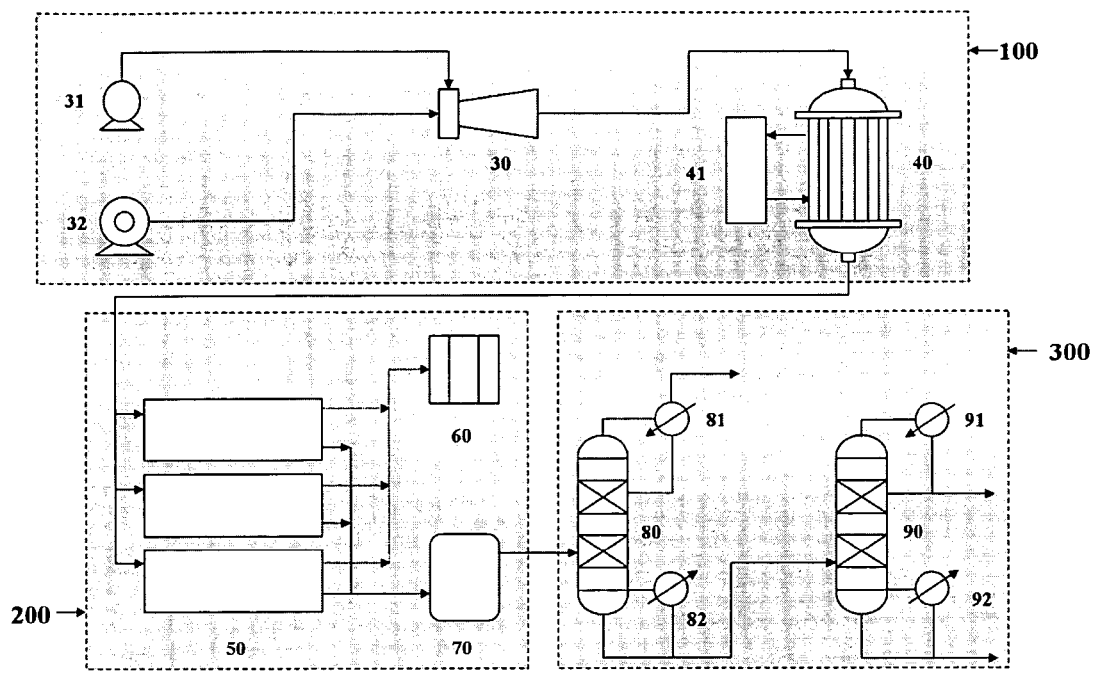
FIG. 1 is a schematic drawing of an embodiment of the manufacturing system for preparing an aromatic dialdehyde according to the present invention.

Hereinafter, the present invention will be more specifically illustrated by the following examples. However, they are only presented as preferable examples, but should not be construed as limiting the scope of the present invention in any way.

The conversion, selectivity, and one-pass yield of the reaction are defined taking by-products into account as follows:

Conversion (mole %)=(the number of mole of reacted starting compound/the number of mole of fed starting compound)×100

Selectivity (mole %)=(the number of mole of each product compound/the number of mole of reacted starting compound)×(the number of carbon atom of each product compound/the number of carbon atom of fed starting compound)×100

One-pass yield (mole %)=(the number of mole of each product compound/the number of mole of fed starting compound)×(the number of carbon atom of each product compound/the number of carbon atom of fed starting compound)×100

PREPARATION EXAMPLE

Preparation Example 1

Ammonium metatungstate hydrate [$(NH4)_6.W_{12}O_{39}.xH_2O$)] was used as a precursor of tungsten oxide. The ammonium metatungstate hydrate was calcined at 650° C. under the air atmosphere for 2 hours to obtain tungsten oxide powder. And, a rubidium nitrate solution having 0.1 mmol/g of rubidium concentration was prepared by dissolving rubidium nitrate ($RbNO_3$) of 1.47 g in water of 98.53 g. Thus diluted solution having the total weight of 10 g was prepared by adding water into the rubidium nitrate solution of 0.4 g, and tungsten oxide powder of 5.564 g was added thereto, followed by heating and agitation in water bath to carry out evaporation. Thus obtained product was dried in an oven of 120° C. for 18 hours, followed by calcining in the furnace of 650° C. under the air atmosphere for 2 hours. The catalyst composition prepared by the above process is $W_{12}Rb_{0.02}Ox$.

Thus obtained catalyst powder was pressurized to prepare pellet, and thus obtained pellet was pulverized and meshed to select catalyst particles having the size of 200 μm. The evaluation experiment was carried out by using the selected catalyst particles.

A continuous flow reactor made of quartz was used for the above experiment. The catalyst of 0.2 g was filled in the quartz reactor, and gas phase oxidation reaction was performed under the following conditions by passing p-xylene and air as reactants:

Reaction pressure: normal pressure
The ratio of gas reactant (volume ratio):
p-xylene/oxygen/nitrogen=0.5/12.5/87 (oxygen/p-xylene=25)
Total feeding rate of gas reactant: 100 cc/min
Reaction temperature: 520, 550, and 580° C.

The test results of the experiment were shown in the following Tables 1 and 2.

The following preparation examples and comparative examples were carried out by using the-catalyst having the particle size of 200 μm prepared in the same method as Preparation Example 1 under the same conditions as the above, except for the amount of fed catalyst, unless mentioned otherwise.

Preparation Example 2

The catalyst having the composition of $W_{12}Rb_{0.03}Ox$ was prepared in the same manner as Preparation Example 1 except using rubidium nitrate solution of 0.6 g.

Preparation Example 3

A cesium nitrate ($CsNO_3$) solution was prepared as a source of cesium. The cesium nitrate solution having 0.1 mmol/g of cesium concentration was prepared by dissolving cesium nitrate of 1.95 g in water of 98.05 g. Thus diluted solution having the total weight of 10 g was prepared by adding water into the cesium nitrate solution of 0.4 g. The catalyst having the composition of $W_{12}Cs_{0.02}Ox$ was prepared in the same manner as Preparation Example 1 except the above.

Preparation Example 4

The catalyst having the composition of $W_{12}Cs_{0.03}Ox$ was prepared in the same manner as Preparation Example 3 except using cesium nitrate solution of 0.6 g.

Preparation Example 5

A sodium nitrate ($NaNO_3$) solution was prepared as a source of sodium. The sodium nitrate solution having 0.1 mmol/g of sodium concentration was prepared by dissolving sodium nitrate of 0.85 g in water of 99.15 g. Thus diluted solution having the total weight of 10 g was prepared by adding water into the sodium nitrate solution of 0.5 g. The catalyst having the composition of $W_{12}Na_{0.025}Ox$ was prepared in the same manner as Preparation Example 1 except the above.

Preparation Example 6

A potassium nitrate ($KNO_3$) solution was prepared as a source of potassium. The potassium nitrate solution having 0.1 mmol/g of potassium concentration was prepared by dissolving potassium nitrate of 1.01 g in water of 98.99 g. The diluted solution having the total weight of 10 g was prepared by adding water into the potassium nitrate solution of 0.4 g. The catalyst having the composition of $W_{12}K_{0.02}Ox$ was prepared in the same manner as Preparation Example 1 except the above.

Preparation Examples 7 to 10

The reactions were carried out by using the same catalyst in the same manner as Preparation Example 1, except that the catalyst amounts filled in the reactor were changed to 0.6, 0.8, 1.0, and 1.5 g, respectively.

Preparation Examples 11 to 13

The reactions were carried out by using the same catalyst as Preparation Example 3 in the same manner as Preparation Example 1, except that the catalyst amounts filled in the reactor were changed to 0.6, 1.0, and 1.2 g, respectively.

Preparation Example 14

An iron nitrate (III) nonahydrate $(FeN_3O_9.9H_2O)$ solution was prepared as a source of iron. The iron nitrate solution having 0.1 mmol/g of iron concentration was prepared by dissolving iron nitrate of 4.04 g in water of 95.96 g. The solution having the total weight of 10 g was prepared by mixing the iron nitrate solution of 1.0 g and the rubidium nitrate solution of 0.4 g of Preparation Example 1, and adding water thereto. The catalyst having the composition of $W_{12}Rb_{0.02}Fe_{0.05}Ox$ was prepared in the same manner as Preparation Example 1 except the above.

Preparation Example 15

The catalyst having the composition of $W_{12}Rb_{0.02}Fe_{0.2}Ox$ was prepared in the same manner as Preparation Example 14, except using the iron nitrate solution of 4.0 g.

Preparation Example 16

The catalyst having the composition of $W_{12}Rb_{0.2}Fe_{0.5}Ox$ was prepared in the same manner as Preparation Example 14, except using the iron nitrate solution of 10 g and the rubidium nitrate solution of 4 g.

Preparation Example 17

The reaction was carried out by using the same catalyst as in Preparation Example 14 in the same manner as Preparation Example 1, except that the catalyst amount filled in the reactor was changed to 0.3 g.

Preparation Example 18

A cerium (III) nitrate $(CeN_3O_9.6H_2O)$ solution was prepared as a source of cerium. The cerium nitrate solution having 0.1 mmol/g of cerium concentration was prepared by dissolving cerium nitrate of 4.34 g in water of 95.66 g. The catalyst having the composition of $W_{12}Rb_{0.02}Ce_{0.3}Ox$ was prepared in the same manner as Preparation Example 14, except using the cerium nitrate solution of 6.0 g. The reaction was carried out in the same manner as Preparation Example 1, except that the catalyst amount filled in the reactor was changed to 0.6 g.

Preparation Example 19

A nickel (II) nitrate $(NiN_2O_6.6H_2O)$ solution was prepared as a source of nickel. The nickel nitrate solution having 0.1 mmol/g of nickel concentration was prepared by dissolving nickel nitrate of 2.91 g in water of 97.09 g. The catalyst having the composition of $W_{12}Rb_{0.02}Ni_{0.1}Ox$ was prepared in the same manner as Preparation Example 14, except using the nickel nitrate solution of 2.0 g. The reaction was carried out in the same manner as Preparation Example 1, except that the catalyst amount filled in the reactor was changed to 1.2 g.

Preparation Example 20

A cobalt (II) nitrate $(CoN_2O_6.6H_2O)$ solution was prepared as a source of cobalt. The cobalt nitrate solution having 0.01 mmol/g of cobalt concentration was prepared by dissolving cobalt nitrate of 2.91 g in water of 97.09 g. The catalyst having the composition of $W_{12}Rb_{0.02}Co_{0.1}Ox$ was prepared in the same manner as Preparation Example 14, except using the cobalt nitrate solution of 2.0 g. The reaction was carried out in the same manner as Preparation Example 1, except that the catalyst amount filled in the reactor was changed to 1.2 g.

Preparation Example 21

A strontium (II) nitrate $(SrN_2O_6)$ solution was prepared as a source of strontium. The strontium nitrate solution having 0.1 mmol/g of strontium concentration was prepared by dissolving strontium nitrate of 2.12 g in water of 97.88 g. The catalyst having the composition of $W_{12}Rb_{0.02}Sr_{0.1}Ox$ was prepared in the same manner as Preparation Example 14, except using the strontium nitrate solution of 2.0 g. The reaction was carried out in the same manner as Preparation Example 1, except that the catalyst amount filled in the reactor was changed to 1.2 g.

Preparation Example 22

A lanthanum (III) nitrate $(LaN_3O_9.6H_2O)$ solution was prepared as a source of lanthanum. The lanthanum nitrate solution having 0.1 mmol/g of lanthanum concentration was prepared by dissolving lanthanum nitrate of 4.33 g in water of 95.67 g. The catalyst having the composition of $W_{12}Rb_{0.02}La_{0.3}Ox$ was prepared in the same manner as Preparation Example 14, except using the lanthanum nitrate solution of 6.0 g. The reaction was carried out in the same manner as Preparation Example 1, except that the catalyst amount filled in the reactor was changed to 1.2 g.

Preparation Example 23

A copper (II) nitrate $(CuN_2O_6.3H_2O)$ solution was prepared as a source of copper. The copper nitrate solution having 0.1 mmol/g of copper concentration was prepared by dissolving copper nitrate of 2.42 g in water of 97.58 g. The catalyst having the composition of $W_{12}Rb_{0.02}Cu_{0.1}Ox$ was prepared in the same manner as Preparation Example 14, except using the copper nitrate solution of 2.0 g. The reaction was carried out in the same manner as Preparation Example 1, except that the catalyst amount filled in the reactor was changed to 0.8 g.

Preparation Example 24

A zinc nitrate $(ZnN_2O_6.6H_2O)$ solution was prepared as a source of zinc. The zinc nitrate solution having 0.1 mmol/g of zinc concentration was prepared by dissolving zinc nitrate of 2.97 g in water of 97.03 g. The catalyst having the composition of $W_{12}Rb_{0.02}Zn_{0.1}Ox$ was prepared in the same manner as Preparation Example 14, except using the zinc nitrate solution of 2.0 g. The reaction was carried out in the same manner as Preparation Example 1, except that the catalyst amount filled in the reactor was changed to 1.2 g.

Preparation Example 25

A zirconyl (IV) nitrate hydrate ($ZrN_2O_7 \cdot xH_2O$) solution was prepared as a source of zirconium. The zirconium nitrate solution having 0.1 mmol/g of zirconium concentration was prepared by dissolving zirconium nitrate of 2.31 g in water of 97.69 g. The catalyst having the composition of $W_{12}Rb_{0.02}Zr_{0.1}Ox$ was prepared in the same manner as Preparation Example 14, except using the zirconium nitrate solution of 2.0 g. The reaction was carried out in the same manner as Preparation Example 1, except that the catalyst amount filled in the reactor was changed to 1.2 g.

Preparation Example 26

A homogeneous precipitation solution having the total weight of 10 g was prepared by mixing the rubidium nitrate solution of 0.2 g of Preparation Example 1 and the potassium nitrate solution of 0.2 g of Preparation Example 5, and adding water thereto. The catalyst having the composition of $W_{12}Rb_{0.01}Ko_{0.01}Ox$ was prepared in the same manner as Preparation Example 1 except the above. The reaction was carried out in the same manner as Preparation Example 1, except that the catalyst amount filled in the reactor was changed to 1.2 g.

Preparation Example 27

A homogeneous precipitation solution having the total weight of 10 g was prepared by mixing the rubidium nitrate solution of 0.2 g of Preparation Example 1 and the cesium nitrate solution of 0.2 g of Preparation Example 3, and adding water thereto. The catalyst having the composition of $W_{12}Rb_{0.01}Cs_{0.01}Ox$ was prepared in the same manner as Preparation Example 1, except the above. The reaction was carried out in the same manner as Preparation Example 1, except that the catalyst amount filled in the reactor was changed to 1.2 g.

Preparation Example 28

The catalyst having the composition of $W_{12}Rb_{0.015}Cs_{0.005}Ox$ was prepared in the same manner as Preparation Example 27 except using the rubidium nitrate solution of 0.3 g and the cesium nitrate solution of 0.1 g. The reaction was carried out in the same manner as Preparation Example 1 except that the catalyst amount filled in the reactor was changed to 1.2 g.

Preparation Example 29

The reaction was carried out by using the same catalyst as in Preparation Example 1. The catalyst of 1.2 g was filled in the reactor, and the reaction was carried out at the temperature of 550° C. for 400 min. Then, the reaction was continued at the temperature of 580° C. for 400 min, 550° C. for 400 min, 600° C. for 400 min, and 550° C. for 400 min, in sequence. The reaction was carried out under the same conditions as Preparation Example 1, except changing the filled amount of catalyst and the temperature.

Comparative Example 1

An ammonium metatungstate solution of 2 mmol/g was prepared by dissolving ammonium metatungstate hydrate of 49.27 g in water of 50.73 g as a source of tungsten. Also, a tartaric acid-antimony solution was prepared as a source of antimony. The tartaric acid-antimony solution having 0.5 mmol/g of antimony concentration was prepared by adding L-tartaric acid of 60 g and antimony(III) oxide ($Sb_2O_3$) of 14.7 g into water of 125.3 g, followed by reflux heating. Further, an iron nitrate (III) nonahydrate ($FeN_3O_9 \cdot 9H_2O$) solution was prepared as a source of iron. The iron nitrate solution having 1 mmol/g of iron concentration was prepared by dissolving iron nitrate of 40.4 g in water of 59.6 g. The iron nitrate solution of 2 g was added into the tartaric acid-antimony solution of 6 g, and the ammonium metatungstate solution of 6 g was added thereto to obtain a homogeneous precipitation solution. Thus obtained solution was heated and agitated in water bath to carry out evaporation. Thus obtained product was dried in an oven of 120° C. for 18 hours, followed by calcining in the furnace of 650° C. under the air atmosphere for 2 hours. The catalyst composition prepared by the above process is $W_{12}Sb_3Fe_2Ox$.

This catalyst of 0.1 g was filled in the reactor, and the reaction was performed under the same temperature condition as Preparation Example 29.

Comparative Example 2

A solution having the total weight of 10 g was prepared by adding water into the tartaric acid solution (0.5 mmol/g) of Comparative Example 1. The tungsten oxide powder (5.564 g) prepared by the same method as Preparation Example 1 was added thereto, followed by heating and agitation in water bath to carry out evaporation. Thus obtained product was dried in an oven of 120° C. for 18 hours, followed by calcining in the furnace of 650° C. under the air atmosphere for 2 hours. The catalyst composition prepared by the above process is $W_{12}Sb_1Ox$.

This catalyst of 0.5 g was filled in the reactor, and the reaction was performed under the same temperature condition as Preparation Example 29.

TABLE 1

| | Amount of catalyst (g) | Temp. (° C.) | p-Xylene Conv. (mol %) | TPAL Selectivity (mol %) | TPAL Yield (mol %) |
|---|---|---|---|---|---|
| Ex. 1 | 0.2 | 550 | 27.2 | 83.2 | 22.7 |
| Ex. 2 | 0.2 | 550 | 20.6 | 80.0 | 16.5 |
| Ex. 3 | 0.2 | 550 | 30.9 | 78.5 | 24.3 |
| Ex. 4 | 0.2 | 550 | 21.1 | 79.1 | 16.7 |
| Ex. 5 | 0.2 | 580 | 64.3 | 69.3 | 44.6 |
| Ex. 6 | 0.2 | 550 | 29.0 | 76.4 | 22.2 |
| Ex. 7 | 0.6 | 550 | 58.9 | 85.0 | 50.0 |
| Ex. 8 | 0.8 | 550 | 71.6 | 81.8 | 58.6 |
| Ex. 9 | 1.0 | 550 | 76.0 | 80.5 | 61.2 |
| Ex. 10 | 1.5 | 550 | 86.8 | 74.0 | 64.3 |
| Ex. 11 | 0.6 | 550 | 62.6 | 82.8 | 51.8 |
| Ex. 12 | 1.0 | 550 | 76.6 | 80.6 | 61.7 |
| Ex. 13 | 1.2 | 550 | 81.4 | 77.1 | 62.8 |
| Ex. 14 | 0.2 | 550 | 71.7 | 75.4 | 54.0 |
| Ex. 15 | 0.2 | 550 | 76.8 | 73.8 | 56.7 |
| Ex. 16 | 0.2 | 550 | 53.6 | 71.0 | 38.1 |
| Ex. 17 | 0.3 | 550 | 82.3 | 73.5 | 60.5 |
| Ex. 18 | 0.6 | 550 | 80.2 | 75.5 | 60.5 |
| Ex. 19 | 1.2 | 550 | 84.8 | 72.9 | 61.8 |
| Ex. 20 | 1.2 | 550 | 81.0 | 76.5 | 61.9 |
| Ex. 21 | 1.2 | 550 | 65.4 | 82.4 | 53.9 |
| Ex. 22 | 1.2 | 550 | 67.3 | 60.2 | 40.5 |
| Ex. 23 | 0.8 | 520 | 68.0 | 66.9 | 45.4 |

TABLE 1-continued

|  | Amount of catalyst (g) | Temp. (° C.) | p-Xylene Conv. (mol %) | TPAL Selectivity (mol %) | TPAL Yield (mol %) |
|---|---|---|---|---|---|
| Ex. 24 | 1.2 | 550 | 75.4 | 72.4 | 54.6 |
| Ex. 25 | 1.2 | 550 | 90.8 | 66.1 | 60.0 |
| Ex. 26 | 1.2 | 520 | 84.8 | 73.4 | 62.3 |
| Ex. 27 | 1.2 | 550 | 73.0 | 74.5 | 54.4 |
| Ex. 28 | 1.2 | 520 | 67.7 | 75.2 | 50.9 |

TPAL: terephthalaldehyde,

TABLE 2

| | Preparation Example 29 | | | Comparative Example 1 | | | Comparative Example 2 | | |
|---|---|---|---|---|---|---|---|---|---|
| Time (min) | p-Xylene Conv. (mol %) | TPAL Selectivity (mol %) | TPAL Yield (mol %) | p-Xylene Conv (mol %) | TPAL Selectivity (mol %) | TPAL Yield (mol %) | p-Xylene Conv. (mol %) | TPAL Selectivity (mol %) | TPAL Yield (mol %) |
| 120 | 86.7 | 74.4 | 64.5 | 81.2 | 68.6 | 55.7 | 82.4 | 58.5 | 48.2 |
| 210 | 85.6 | 74.4 | 63.7 | 82.5 | 67.9 | 56.0 | 82.0 | 56.8 | 46.6 |
| 300 | 85.3 | 74.7 | 63.7 | 83.6 | 67.0 | 56.0 | 82.6 | 56.8 | 46.9 |
| 390 | 84.7 | 74.6 | 63.2 | 84.8 | 67.1 | 56.9 | 83.9 | 57.3 | 48.1 |
| 920 | 83.7 | 74.5 | 62.3 | 90.3 | 61.5 | 55.5 | 81.0 | 53.4 | 43.3 |
| 1010 | 83.6 | 74.4 | 62.2 | 90.7 | 61.5 | 55.8 | 82.2 | 52.7 | 43.3 |
| 1100 | 83.6 | 74.1 | 61.9 | 90.8 | 60.4 | 54.9 | 82.5 | 52.3 | 43.1 |
| 1720 | 83.9 | 75.3 | 63.1 | 92.7 | 57.8 | 53.6 | 88.0 | 46.8 | 41.1 |
| 1810 | 83.8 | 75.3 | 63.0 | 93.2 | 58.3 | 54.3 | 88.8 | 46.3 | 41.1 |
| 1900 | 83.5 | 75.8 | 63.3 | 93.6 | 58.4 | 54.6 | 89.4 | 45.7 | 40.9 |
| 1990 | 83.6 | 75.7 | 63.3 | 93.5 | 58.3 | 54.5 | 89.5 | 45.3 | 40.5 |

EXAMPLES

Example 1

An aqueous ammonium metatungstate solution in a concentration of 2 mmol/g was prepared as a source of tungsten. The aqueous solution was heated under stirring in water bath to be evaporated and dried, which was then dried at 120° C. over 18 h. The residue was calcined at 650° C. under air atmosphere for 2 h to give an tungsten oxide. 30 g of the tungsten oxide was introduced into 250 mL of PP bottle, 70 g of ethanol was added thereto as a dispersing agent, and then mixed. A zirconia ball was introduced, and wet milling was carried out for 3 h by using a milling device.

The slurry was introduced into a vessel having 60 g of a-alumina carrier SA5205 (Norton Co., 5 mm sphere) previously heated to 120° C., and then heated under stirring in water bath to be evaporated and dried. The residue was finally dried at 120° C. for 18 h, and calcined at 650° C. under air atmosphere for 2 h. Thus obtained catalyst occupies 30.5% with respect to the total weight of the catalyst, and so has the composition of 30.5 wt % WOx/SA5205.

The oxidation reaction of p-xylene was carried out in a bench scale experiment by using the above catalyst. The oxidation reactor in the above experiment is a catalytic reactor of the type of fixed bed, and the reaction temperature was controlled by a molten salt. The flow of p-xylene was controlled to 2.7 cc/hr by using a syringe pump, and the p-xylene was mixed with air after it passed through a vaporizer previously heated to 150° C. The mixture of p-xylene and air (total flow 120 cc/min) was heated to 200° C. by a preheater, and introduced into a reactor.

The reaction temperature of the oxidation reactor was controlled to 560° C., and after the gas phase oxidation reaction, the resulting mixture was introduced into a condenser of room temperature (about 20° C.) through a transfer line heated to 350° C.

Among the reaction mixture introduced into the condenser, terephthalaldehyde and other condensable compounds were condensed and separated as a solid (including a trace amount of liquid), and the other gas phase compounds are transferred to an absorption vessel. The absorption vessel was filled with methanol to dissolve the reaction product not recovered, and the residual gases were vented.

Crude terephthalaldehyde condensed as a solid in the condenser was recovered.

A part of the mixture resulted from the gas phase oxidation reaction was transferred to "on-line GC" and analyzed. The analysis results of the "on-line GC" are shown in the following Table 3.

Example 2

The catalyst was prepared in the same manner as Example 1 except that 30 g of $W_{12}Rb_{0.02}Ox$ powder prepared in Preparation Example 1 was used instead of the tungsten oxide.

The finally obtained catalyst occupies 30.6% to the total weight of the catalyst, and so has the composition of 30.6 wt % $W_{12}Rb_{0.02}Ox/SA5205$.

The reaction was carried out at 580° C. in the same manner as Example 1, and the results are shown in the following Table 3.

TABLE 3

| | Conversion of | Selectivity (mol %) | | | | | | | TPAL Yield |
|---|---|---|---|---|---|---|---|---|---|
| | | TPAL | P-TOAL | CO | $CO_2$ | BAL | 4-HBA | Others | |
| Ex. 1 | 81.1 | 68 | 4.8 | 6.9 | 11.8 | 2.0 | 1.7 | 4.5 | 55.1 |
| Ex. 2 | 82.3 | 67.5 | 4.5 | 6.6 | 12.8 | 2.6 | 1.7 | 4.3 | 55.6 | tolualdehyde, BAL means benzaldehyde, 4-CBA means 4-carboxybenzaldehyde, and 4-HBA means 4-hydroxybenzaldehyde.

Example 3

Figure 2:
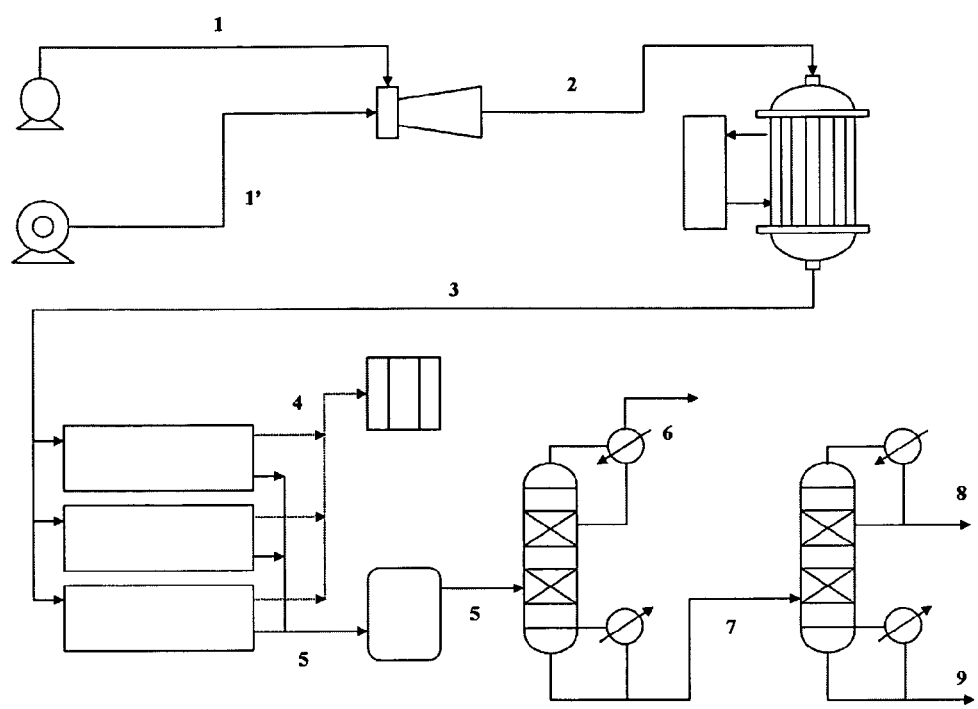
FIG. 2 is a schematic process diagram showing the simulation process according to the Example 2 of the present invention.

A simulation experiment regarding the preparation of aromatic dialdehyde was carried out by using ASPEN-Plus. The flow rates of the reactants were decided to 306 kg/hr for p-xylene, 2546 kg/hr for oxygen, and 7581 kg/hr for nitrogen. When the reactants were introduced into the protocol as depicted in FIG. 2 in the flow rates as described above, the temperature condition of each gas flow discharged from the reactor, condenser, first distillation column, and second distillation column was shown in the following Table 4 with the flow rate of each component in each gas flow.

The compositions of Table 1 which were obtained from the experiment of Example 1 were used as the compositions discharged from the reactor. The material balance between switch condenser and distillation column was obtained by simulation according to a thermodynamic equation.

TABLE 4

| | | Stream No. | | | | | | | | |
|---|---|---|---|---|---|---|---|---|---|---|
| | | 1 | 1' | 2 | 3 | 4 | 5 | 6 | 7 | 8 | 9 |
| Temperature (° C.) | | 160.0 | 180.0 | 25.0 | 580.0 | 30.0 | 130.0 | 76.4 | 173.2 | 169.9 | 198.8 |
| Pressure (atm) | | 4.0 | 1.6 | 1.5 | 1.0 | 1.0 | 1.0 | 0.1 | 0.1 | 0.1 | 0.1 |
| Flow rate (Kg/hr) | P-xylene | 306.3 | 0.0 | 306.3 | 29.7 | 29.7 | 3.8 | 3.8 | 0.0 | 0.0 | 0.0 |
| | TPAL | 0.0 | 0.0 | 0.0 | 260.0 | 260.0 | 259.0 | 0.0 | 259.0 | 255.9 | 3.1 |
| | P-TOAL | 0.0 | 0.0 | 0.0 | 10.8 | 10.8 | 10.2 | 10.2 | 0.0 | 0.0 | 0.0 |
| | CO | 0.0 | 0.0 | 0.0 | 46.3 | 46.3 | 0.0 | 0.0 | 0.0 | 0.0 | 0.0 |
| | CO2 | 0.0 | 0.0 | 0.0 | 120.9 | 120.9 | 0.0 | 0.0 | 0.0 | 0.0 | 0.0 |
| | BAL | 0.0 | 0.0 | 0.0 | 6.4 | 6.4 | 5.2 | 5.2 | 0.0 | 0.0 | 0.0 |
| | O2 | 0.0 | 2545.9 | 2545.9 | 2246.7 | 2246.7 | 0.1 | 0.1 | 0.0 | 0.0 | 0.0 |
| | N2 | 0.0 | 7580.8 | 7580.8 | 7580.8 | 7580.8 | 0.1 | 0.1 | 0.0 | 0.0 | 0.0 |
| | H2O | 0.0 | 0.0 | 0.0 | 124.9 | 124.9 | 22.5 | 22.5 | 0.0 | 0.0 | 0.0 |
| | 4-CBA | 0.0 | 0.0 | 0.0 | 0.9 | 0.9 | 0.9 | 0.0 | 0.9 | 0.0 | 0.9 |
| | BA | 0.0 | 0.0 | 0.0 | 0.1 | 0.1 | 0.1 | 0.1 | 0.0 | 0.0 | 0.0 |
| | 4-HBA | 0.0 | 0.0 | 0.0 | 5.2 | 5.2 | 5.2 | 0.0 | 5.2 | 0.2 | 5.0 |
| | HQ | 0.0 | 0.0 | 0.0 | 0.2 | 0.2 | 0.2 | 0.0 | 0.2 | 0.0 | 0.2 |
| | TPA | 0.0 | 0.0 | 0.0 | 0.2 | 0.2 | 0.2 | 0.0 | 0.2 | 0.0 | 0.2 |
| Total Flow rate | | 306.3 | 10126.7 | 10433.0 | 10433.0 | 10433.0 | 307.5 | 42.1 | 265.5 | 256.2 | 9.3 |

In the above Table 4, the number of gas flow corresponds to that of gas flow described in each protocol of FIG. 2. Further, TPAL means terephthalaldehyde, p-TOAL means p-tolualdehyde, BAL means benzaldehyde, 4-CBA means 4-carboxybenzaldehyde, BA means benzoic acid, 4-HBA means 4-hydroxybenzaldehyde, HQ means hydroquinone, and TPA means terephthalic acid.

EFFECT OF THE INVENTION

The process for preparing an aromatic dialdehyde according to the present invention is simple, effective, and advantageous in that the highly pure aromatic dialdehyde can be continuously prepared.

The invention claimed is:

1. A method for preparing an aromatic dialdehyde, comprising:
    a) a step of gas phase oxidation reaction for preparing an aromatic dialdehyde by oxidizing dimethylbenzene in a gaseous phase;
    b) a step of separation for selectively recovering crude aromatic dialdehyde of molten phase by cooling and condensing a reaction product from the gas phase oxidation reaction, and heating to melt it down; and
    c) a step of purification for obtaining highly pure aromatic dialdehyde by purifying the crude aromatic dialdehyde.

2. The method of claim 1, wherein the dimethylbenzene is one or more selected from the group consisting of o-xylene, m-xylene and p-xylene.

3. The method of claim 1, wherein the gas phase oxidation reaction is carried out by using oxygen or oxygen-containing air as the gas phase oxidant.

4. The method of claim 1, wherein the reaction temperature of the gas phase oxidation reaction ranges from 350 to 600° C.

5. The method of claim 1, wherein the gas phase oxidation reaction is carried out in the presence of a solid catalyst comprising at least one of tungsten and molybdenum as an active component.

6. The method of claim 5, wherein the solid catalyst comprises as an active component the compound of the following formula (I):

$$W_aX_bY_cO_x \qquad (1)$$

wherein
W represents a tungsten atom,
X represents one or more alkali metals selected from the group consisting of Li, Na, K, Rb, and Cs,
Y represents one or more elements selected from the group consisting of Fe, Co, Ni, Cu, Mn, Re, Cr, V, Nb, Ti, Zr, Zn, Cd, Y, La, Ce, B, Al, Sn, Mg, Ca, Sr, and Ba,
O stands for an oxygen atom,
a, b, c and x each represent the atomic number of W, X, Y and oxygen atom, respectively,
the ratio of a:b:c is 12:0.001~1:0~5, and
x is a value determined by the oxidation state of W, X, and Y.

7. The method of claim 1, wherein the aromatic dialdehyde prepared from the gas phase oxidation reaction is one or more selected from the group consisting of phthaldialdehyde, isophthalaldehyde and terephthalaldehyde.

8. The method of claim 1, wherein the step of separation uses a switch condenser of which the temperature control is possible.

9. The method of claim 8, wherein the step of separation is carried out in a continuous manner by using two or more switch condensers wherein cooling and heating are repeated in turns, and each of cooling and heating is achieved by passing a heat transfer oil through a tube bundle equipped with a heat transfer fin in the switch condenser.

10. The method of claim 1, wherein the temperature of the switch condenser at the cooling mode ranges from 5 to 70° C., and that of the switch condenser at the heating mode ranges from 110 to 200° C.

11. The method of claim 1, wherein the melting stage in the step of separation b) is carried out in the state that the inside of the switch condenser is purged with one or more inert gases selected from the group consisting of nitrogen, argon, helium and $CO_2$.

12. The method of claim 1, wherein the step of purification c) uses a distillation device comprising, i) first distillation column to remove impurities having a low boiling point, and ii) second distillation column connected with the first column in series to recover the aromatic dialdehyde.

13. The method of claim 12, wherein the step of purification c) comprises
   i) removing impurities having a low boiling point from top of the first distillation column by heating the first column to 74~79° C., and
   ii) recovering the aromatic dialdehyde from top of the second distillation column by heating the second column connected with the first column in series to 165~170° C., and
   iii) discharging the compounds having a high boiling point piled up at bottom of the second column.

14. A manufacturing system for preparing an aromatic dialdehyde comprising, a) a part for gas phase oxidation reaction b) a part for separation, and c) a part for purification, wherein
   a) the part for gaseous phase oxidation reaction comprises a feeder of dimethylbenzene, a feeder of gas phase oxidant, and a reactor where the gas oxidation reaction occurs,
   b) the part for separation comprises a switch condenser, and
   c) the part for purification comprises first distillation column for removing impurities having a low boiling point, and second distillation column for recovering highly pure aromatic dialdehyde.

* * * * *